United States Patent
Farber et al.

[11] Patent Number: 5,980,728
[45] Date of Patent: *Nov. 9, 1999

[54] DIAGNOSTIC METHOD AND APPARATUS FOR SOLID ELECTROLYTE GAS ANALYZER

[75] Inventors: Boris Y. Farber, Solon; Michael G. O'Neill, Wooster; Michael T. Estvander, Wadsworth; James W. Thomson, Akron, all of Ohio

[73] Assignee: Rosemont Analytical Inc., LaHabra, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,140

[22] Filed: Sep. 24, 1996

[51] Int. Cl.$^6$ ................................. G01N 27/407
[52] U.S. Cl. .................. 205/784; 204/401; 204/421; 204/424; 205/784.5
[58] Field of Search .............. 204/401, 421–429; 205/783.5, 784, 784.5, 785

[56] References Cited

U.S. PATENT DOCUMENTS

| | | | |
|---|---|---|---|
| 3,360,719 | 12/1967 | Saito et al. | 324/31 |
| 3,400,054 | 9/1968 | Ruka et al. | 204/1 |
| 3,661,748 | 5/1972 | Blackmer | 204/195 |
| 3,718,568 | 2/1973 | Neuwelt | 204/195 P |
| 3,862,895 | 1/1975 | King et al. | 204/195 R |
| 3,903,853 | 9/1975 | Kizler et al. | 123/32 |
| 3,915,828 | 10/1975 | Cleary et al. | 204/195 S |
| 3,928,161 | 12/1975 | McIntyre et al. | 204/195 |
| 4,071,817 | 1/1978 | Bahl | 324/30 R |
| 4,088,543 | 5/1978 | Ruka | 204/1 T |
| 4,094,186 | 6/1978 | Wessel | 73/1 G |
| 4,138,881 | 2/1979 | Isenberg | 73/27 |
| 4,158,166 | 6/1979 | Isenberg | 324/29 |
| 4,167,163 | 9/1979 | Moder | 123/119 |
| 4,189,367 | 2/1980 | Connery et al. | 204/195 G |
| 4,223,549 | 9/1980 | Kitzinger | 204/401 |
| 4,231,733 | 11/1980 | Hickam et al. | 431/76 |

(List continued on next page.)

FOREIGN PATENT DOCUMENTS

| | | |
|---|---|---|
| 2 194 056 | 2/1988 | United Kingdom . |
| 2 219 093 | 11/1989 | United Kingdom . |
| 2 252 167 | 7/1992 | United Kingdom . |
| 2 285 314 | 7/1995 | United Kingdom . |

OTHER PUBLICATIONS

"Probe Type Oxygen Analyzer Package With Digital Electronics", Rosemount Analytical Inc. Instruction Bulletin IB–106–101U, Model 218 (Jun. 1989), p. 1–1 to 8–5.

"Study of Solid Electrolyte Polarization by a Complex Admittance Method", *J. Phys. Chem. Solids*, by J.E. Bauerle, vol. 30, (1969) month unavailable p. 2657–2670.

"Electrode Kinetics at the Palladium/Ceramic Oxide Electrolyte Interface", *J. Electrochem. Soc.*, by S.P.S. Badwal and H.J. de Bruin, vol. 129, No. 9 (Sep. 1982), p. 1921–1928.

"Impedance Characteristics of Platinum Electrodes on Yttria–Stabilized Zirconia", *Ber. Bunsenges Phys. Chem.*, by J. Van Herle and A.J. McEvoy, vol. 97, No. 3 (1993) month unavailable, p. 470–474.

(List continued on next page.)

Primary Examiner—T. Tung
Attorney, Agent, or Firm—Westman, Champlin & Kelly, P.A.

[57] ABSTRACT

A solid electrolyte gas analyzer is equipped with a diagnostic circuit that intermittently measures an impedance of the solid electrolyte measurement cell as an indication that the cell is in need of calibration or replacement. The diagnostic operation is performed on the cell in situ, i.e., while the solid electrolyte cell is exposed to the gas to be measured and heated to a controlled elevated temperature. Preferably the cell impedance is measured at a predetermined frequency by injecting a modulated current through the cell and measuring the resulting voltage drop.

18 Claims, 9 Drawing Sheets

U.S. PATENT DOCUMENTS

| | | | |
|---|---|---|---|
| 4,279,142 | 7/1981 | McIntyre | 73/1 G |
| 4,462,872 | 7/1984 | Nelson | 204/1 T |
| 4,468,608 | 8/1984 | Rolfe | 324/51 |
| 4,532,013 | 7/1985 | Dietz et al. | 204/401 |
| 4,537,661 | 8/1985 | Lee et al. | 204/1 T |
| 4,626,338 | 12/1986 | Kondo et al. | 204/425 |
| 4,777,444 | 10/1988 | Bejk et al. | 324/439 |
| 4,822,456 | 4/1989 | Bryan | 204/1 T |
| 4,829,253 | 5/1989 | Koluvek | 324/438 |
| 5,059,908 | 10/1991 | Mina | 324/444 |
| 5,268,852 | 12/1993 | Forsythe et al. | 364/482 |
| 5,353,200 | 10/1994 | Bodin et al. | 361/816 |
| 5,392,643 | 2/1995 | O'Kennedy et al. | 73/118.1 |
| 5,469,070 | 11/1995 | Koluvek | 324/713 |
| 5,547,552 | 8/1996 | Hasegawa et al. | 204/425 |

OTHER PUBLICATIONS

"Complex–Impedance Analysis for the Development of Zirconia Oxygen Sensors", *Solid State Ionics*, by N. Matsui, vol. 3/4 (1981) month unavailable, p. 525–529.

"Microstructure of Pt Electrodes and its Influence on the Oxygen Transfer Kinetics", *Solid State Ionics*, by S.P.S. Badwal and F.T. Ciacchi, vol. 18 & 19 (1986) month unavailable, p. 1054–1060.

"7875—In–Situ Zirconium Oxygen Analyzer", Early version of manual by Leeds& Northrup (1979) month unavailable.

"Something Extra in Performance, In–Situ Zirconia Oxygen Analyzer", Advertising Sheet by Leeds & Northrup (1979) month unavailable.

"7875 In–Situ Zirconia Oxygen Analyzer" Sales Brochure HC3.1122 (6 pages, published about 1979) month unavailable.

Model 132 Oxygen Analyzer Package with Digital Electronics, Instruction Bulletin IB–106–106A (Jun. 1989) Rev. 6, by Rosemount Analytical Inc.

"Mini Probe Oxygen Analyzer with Digital Electronics Package, for Small Packaged Boilers", Descriptive Bulletin 106–106A, by Rosemount Analytical Inc., Sep. 1989, p. 1–4.

"Hagan Probe Type Excess Oxygen/Excess Combustibles Analyzer", Descriptive Bulletin 106–104, by Rosemount Analytical Inc., p. 1–4. date unavailable.

"World Class 3000 Oxygen Analyzer Package", Descriptive Bulletin 106–300, by Rosemount Analytica Inc., (Jul. 1990) p. 1–6.

"Oxygen Analyzer Package with Analog Electronics (FM Approved)", Descriptive Bulletin 106–101, by Rosemount Analytical Inc., (Jul. 1990) p. 1–4.

"7875 In–Situ Zirconia Oxygen Analyzer", Manual 277141 Rev. A1, by Leeds & Northrup (1979) month unavailable.

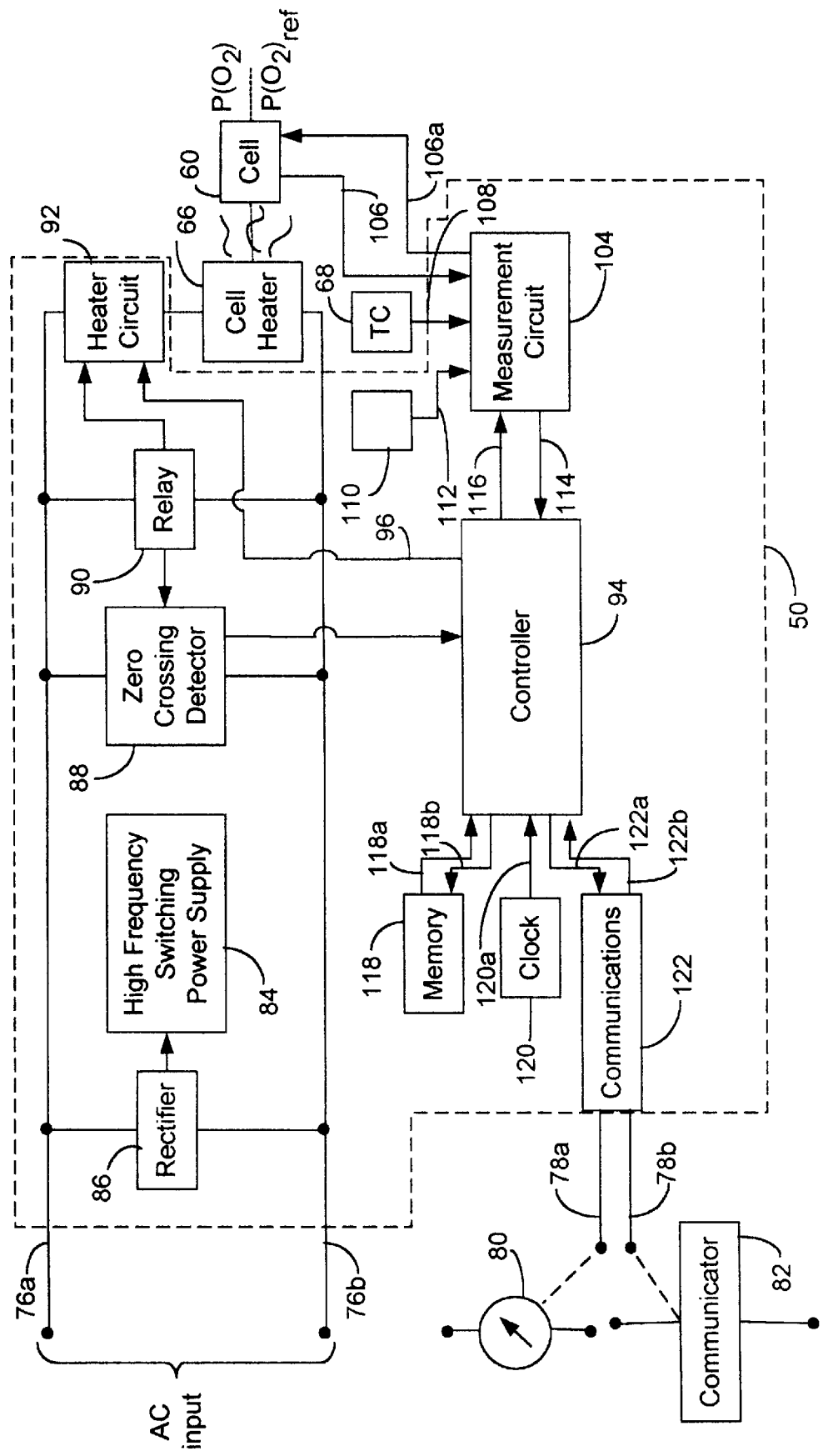

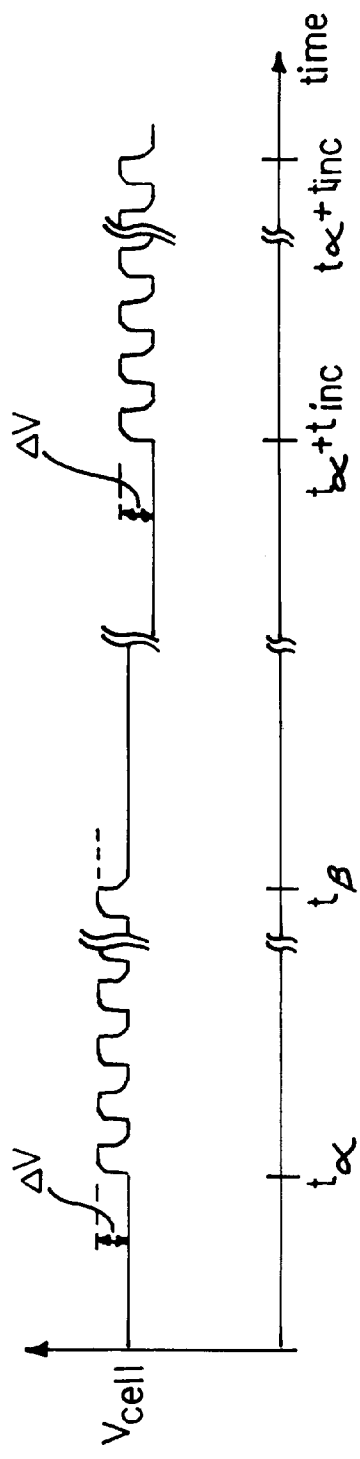
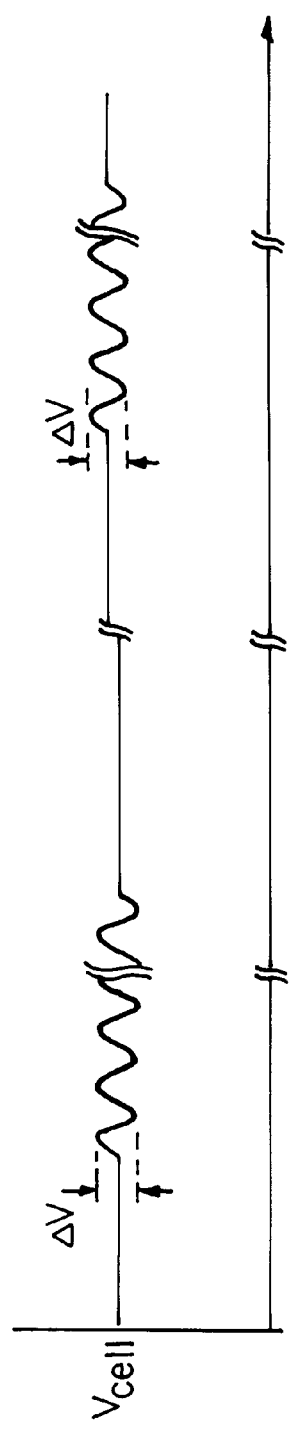
Fig. 8a
Fig. 8b

DIAGNOSTIC METHOD AND APPARATUS FOR SOLID ELECTROLYTE GAS ANALYZER

CROSS REFERENCE TO RELATED APPLICATIONS

This application relates to co-pending U.S. patent applications entitled "Solid Electrolyte Gas Analyzer With Improved Circuit and Housing Configuration", Ser. No. 08/719,127, and "Passive Cell Protection For Solid Electrolyte Gas Analyzer", Ser. No. 08/928,245, both incorporated herein by reference, assigned to the same assignee as the present application and filed on even date herewith.

BACKGROUND OF THE INVENTION

The present invention relates generally to the segment of the field of gas analysis instrumentation that involves the use of solid electrolyte cells to measure gaseous species. More specifically, the invention relates to a novel diagnostic method and apparatus for use with a heated solid electrolyte cell to assess the condition of such cell. As used herein, the term solid electrolyte cell means a quantity of the solid electrolyte, for example zirconia-yttria $((ZrO_2)_{(1-x)}(Y_2O_3)_x)$, and porous electrical contacts or electrodes connected thereto, usually made of platinum or other suitable materials.

Gas analyzers having a probe with a solid electrolyte cell to measure gaseous oxygen are well known. See, for example, U.S. Pat. Nos. 3,400,054 and 3,928,161, incorporated herein by reference. Another example is the World Class 3000 Oxygen Analyzer sold by Rosemount Analytical Inc. of Orrville, Ohio, available with replacement cells under part no. 4847B61G01/02/03. A common application for such analyzers is the measurement of gaseous oxygen in a flue or duct such as a smokestack. At a given elevated temperature, the solid electrolyte cell generates an EMF $V_{cell}$ as a function of the concentration of oxygen (or other gaseous specie) exposed to the cell. $V_{cell}$ can be approximated by the Nernst equation:

$$V_{cell} = C + S \cdot \log\{P(O_2)/P(O)_{REF}\}, \quad (EQ. 1)$$

where C is a cell constant, S is a cell slope which is a function of cell temperature T, and $P(O_2)$ and $P(O_2)_{REF}$ are the oxygen partial pressure at a measurement and reference end, respectively, of the solid electrolyte cell. Actual solid electrolyte cells deviate from Equation 1 to some extent.

It is also known for solid electrolyte analyzers to include analog or digital electronic circuitry in a housing separate from the probe that measures $V_{cell}$ and provides an analyzer output indicative of the gaseous species concentration. The probe is configured with a heater and thermocouple, controlled by circuitry in the separate housing, to maintain the solid electrolyte cell at a constant elevated temperature (e.g., $T \approx 750°$ C.).

It is also known to provide a pneumatic tube in a gas analyzer probe to supply reference gas with a known oxygen content $P(O_2)_{REF}$ to a reference side of the cell, and to provide another pneumatic tube that can when desired supply a calibration gas having an oxygen content $P(O_2)_{CAL}$ to a measuring side of the cell. Usually the pneumatic tube supplying the calibration gas is closed and the measuring side of the cell contacts the gas of interest that is to be measured for oxygen content.

It is further known that solid electrolyte cells can degrade over their useful life, experiencing an increase in cell resistance and also experiencing a decrease in $V_{cell}$.

An object of the invention is to provide an in situ indication of the condition of the solid electrolyte cell, without having to supply specialized calibration gas to the analyzer or otherwise interrupt the operation of the analyzer. Cell condition information can include time remaining to calibration, an out-of-calibration indication, time remaining to replacement, and a need-to-replace indication.

Other objects of the invention will become apparent from the detailed description of the invention and the accompanying drawings.

BRIEF SUMMARY OF THE INVENTION

The invention provides an indication of the condition of a solid electrolyte cell in a gas analyzer also having a heater disposed proximate the cell. The cell provides a cell output as a function of a gas of interest. An analyzer circuit provides an analyzer output as a function of the cell output and includes a heater circuit and a measurement circuit. The heater circuit couples to the heater to maintain the cell at an elevated temperature. The measurement circuit couples to the cell, and has a diagnostic circuit to measure a characteristic of the cell while the cell is exposed to the gas of interest. The cell characteristic is indicative of the cell condition, and preferably is an impedance of the cell measured at a particular frequency by injecting a known modulated current through the cell and monitoring the resulting voltage change. The cell condition can include a time remaining to the next recommended calibration, a time remaining to recommended cell replacement, and indications that the cell is in need of calibration or replacement. Non-negative values of both time-to-calibration and time-to-replacement means that the analyzer output is probably within a specified accuracy tolerance. Negative values of either trigger the need-to-calibrate or -replace indications, respectively.

BRIEF DESCRIPTION OF THE DRAWINGS

FIG. 1 is a block diagrammatic schematic of a preferred analyzer circuitry.

FIGS. 8a and 8b are waveforms associated with different diagnostic circuits for solid electrolyte gas analyzers according to the invention.

Figure 2A:
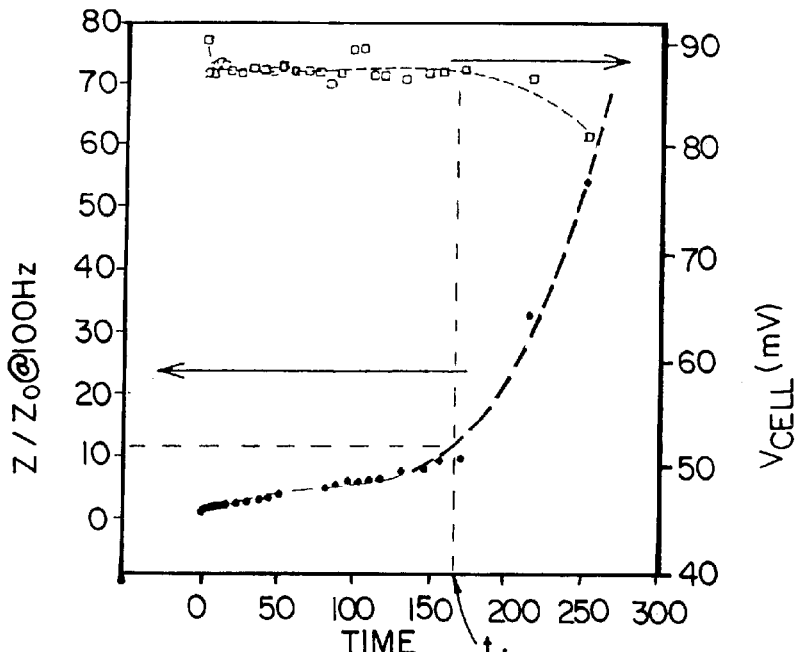
FIGS. 2a and 2b are graphs showing the performance of a heated solid electrolyte cell as a function of time.

For convenience, items in the figures having the same reference symbol are the same or serve the same or a similar function.

DETAILED DESCRIPTION OF THE PREFERRED EMBODIMENTS

FIG. 1 shows a block diagram of a preferred analyzer circuit 50 in a solid electrolyte analyzer 40 according to the invention. Circuit 50 is energized by AC line input provided across lines 76a, 76b by a remote source. Circuit 50 controls a cell heater 66 which is arranged to heat a solid electrolyte cell 60. Cell heater 66 is preferably of conventional design, formed of a length of nichrome wire helically wrapped around a quartz support cylinder. A thermocouple 68 or other high temperature sensing device detects the temperature of cell 60, and preferably also of heater 66, for monitoring and feedback control purposes. Circuit 50 monitors a cell output $V_{cell}$ from cell 60 and a temperature T from thermocouple 68, and communicates a parameter indicative of $P(O_2)$ over lines 78a, 78b to a meter 80 or a communicator 82. Communicator 82 can also send commands and other signals to circuit 50, preferably using HART® or fieldbus protocol over lines 78a, 78b.

To provide low voltage DC power to its various circuit components, circuit 50 uses a switching power supply 84 coupled to lines 76a, 76b through a rectifier 86. Co-pending application "Solid Electrolyte Gas Analyzer With Improved Circuit and Housing Configuration", referenced above, provides further details on this power supply.

Also coupled across lines 76a, 76b in parallel with rectifier 86 are a zero crossing detector 88, a relay 90, and a series combination of a heater circuit 92 with the cell heater 66, details of which are also found in the referenced co-pending application.

A controller 94 controls heater circuit 92 over line 96 to maintain thermocouple 68, and hence cell 60, at a specified elevated temperature. Controller 94 also couples to a measurement circuit 104 over lines 114, 116. Measurement circuit 104 receives the output of cell 60 over a line 106, the output of thermocouple 68 over a line 108, and the output of a local temperature sensor 110 over a line 112. These outputs are communicated to controller 94 over a line 114. The output at line 112 indicates the temperature inside an electronics housing (not shown) that houses circuit 50. Controller 94 uses the sensor 110 output as an indication of cold junction temperature to correct the raw EMF output from thermocouple 68 in calculating cell temperature T. Sensor 110 is preferably a model AD590 semiconductor current source available from Analog Devices Inc., Norwood, Mass., but can be any other suitable temperature sensor such as a thermistor.

According to an aspect of the invention, controller 94 can command measurement circuit 104 over a line 116 to perform a diagnostic check of cell 60 over a line 106a while the cell 60 is in situ, i.e., fully installed in the flue and exposed to the flue gas. The diagnostic check preferably measures the impedance Z of cell 60 at one or more selected frequencies, and this value is communicated to controller 94 over line 114.

Controller 94 also communicates with a non-volatile memory circuit 118, a clock circuit 120, and a communications circuit 122 over lines 118a, 118b, a line 120a, and lines 122a, 122b respectively. Memory 118 holds an equation similar to EQ. 1 relating measured $V_{cell}$ and cell temperature T to oxygen content $P(O_2)$. Memory 118 also holds information regarding the predicted behavior of the cell impedance Z as a function of time, Z(t). Memory 118 further holds information regarding a calibration criterion which predicts when cell 60 will fail to achieve a specified accuracy, thereby requiring the user to calibrate cell 60. Memory 118 also preferably holds information regarding a replacement criterion which predicts when cell 60 will fail to function reliably, thereby requiring replacement of cell 60. Controller 94 uses the measured cell impedance Z, the predicted cell impedance function Z(t), and the calibration and replacement criteria to calculate a time remaining to calibration $t_{TTc}$ and a time remaining to replacement $t_{TTR}$. Further, if controller 94 calculates that the time for calibration or the time for replacement has been exceeded, controller 94 can provide warning indications for each such condition.

The diagnostic function Z(t) is preferably obtained from an analysis of aging tests on a large number of solid electrolyte cells substantially identical to the cell 60 used in analyzer 40. By monitoring the output error of such cells one can establish criteria involving the diagnostic parameter Z and/or the elapsed time t which predict when the cell output error will exceed a specified value (requiring calibration) and when the cell 60 will no longer be capable of reliable operation (requiring replacement).

Figure 2B:
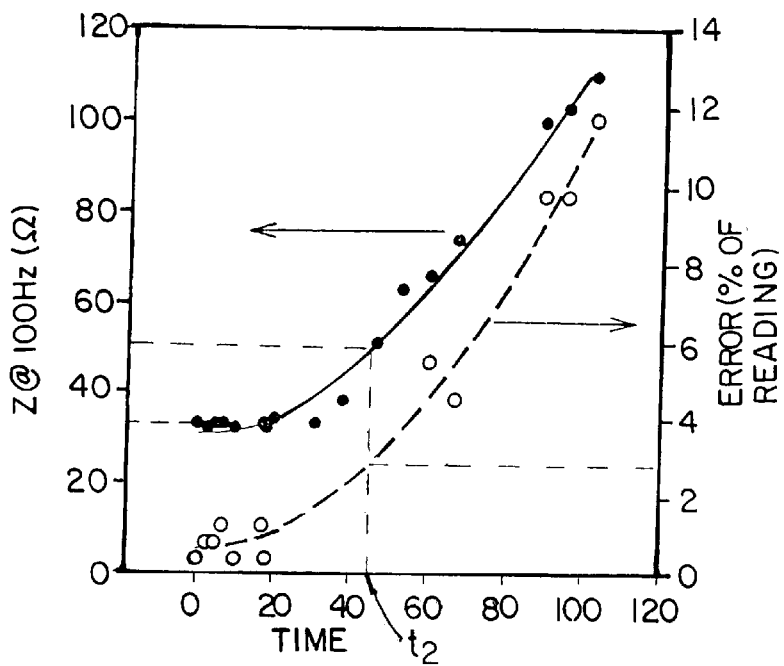

It is known that solid electrolyte cells can have complex impedances. See, e.g., N Matsui, Solid State Ionics 3/4 (1981), pp. 525–529. The present invention recognizes that measuring the cell impedance at substantially a single frequency can be adequate to assess the condition of the cell. FIGS. 2a and 2b show accelerated lifetime test data for a particular type of solid electrolyte cell in a high sulfur environment. In both figures the diagnostic data points are shown by darkened circles and use the left vertical scale and cell performance data points are shown by outlined circles or squares and use the right vertical scale. The x-axis of both figures is elapsed time of the tested cell maintained at a temperature of 750° C., with values given in days.

In FIG. 2a Z represents measured cell impedance using a 100 Hz square wave injection current and $Z_0$ is such measured impedance at time t=0. FIG. 2a demonstrates how the dimensionless relative cell impedance $Z/Z_0$ increases with elapsed time. Concurrently, cell output $V_{cell}$ decreases. The rate of decrease in $V_{cell}$ and the rate of increase in Z are relatively slow before time t=$t_1$ and become more rapid after time t=$t_1$. At time $t_1$, the relative impedance $Z/Z_0$ is approximately 10 for the particular type of solid electrolyte cell tested. Therefore, for this particular type of cell, the following replacement criterion can be used to indicate the need for cell replacement:

$$Z/Z_0 > 10. \tag{EQ. 2}$$

In FIG. 2b cell impedance Z is measured in the same way as in FIG. 6a, but cell performance is measured by the error in the value $P(O_2)$ calculated from Equation 1 above. I.e., the error plotted is $$\text{Error} = 100\% \cdot [P(O_2)_{Actual} - P(O_2)_{Calculated}]/P(O_2)_{Actual} \tag{EQ. 3}$$

The cell impedance increase is clearly accompanied by an increased measurement error. An example of a specified accuracy for a solid electrolyte analyzer is 3% of reading. The measurement error in FIG. 6b begins to exceed about 3% at time $t_2$, at which time Z is about 20 Ω above its original value, $Z_0$. Therefore, for the particular cells tested for this example, the following calibration criterion can be used to indicate that the cell output may be out of tolerance and that the sensor should be calibrated:

$$Z \geq Z_0 + 20 \text{ Ω} \tag{EQ. 4}$$

The cell impedance Z shown in FIGS. 6a and 6b can be approximated by the following function of time t:

$$\sqrt{Z(t)} = a + b \cdot \sqrt{t} \qquad (EQ.\ 5)$$

or $$Z(t) = (a + b \cdot \sqrt{t})^2 \qquad (EQ.\ 6)$$

and solving Equation 5 or 6 for t yields $$t = [\sqrt{Z(t)} - a]^2 / b^2 \qquad (EQ.\ 7)$$

where coefficients a and b in Equations 5–7 can vary somewhat from one cell to another.

Figure 3A:
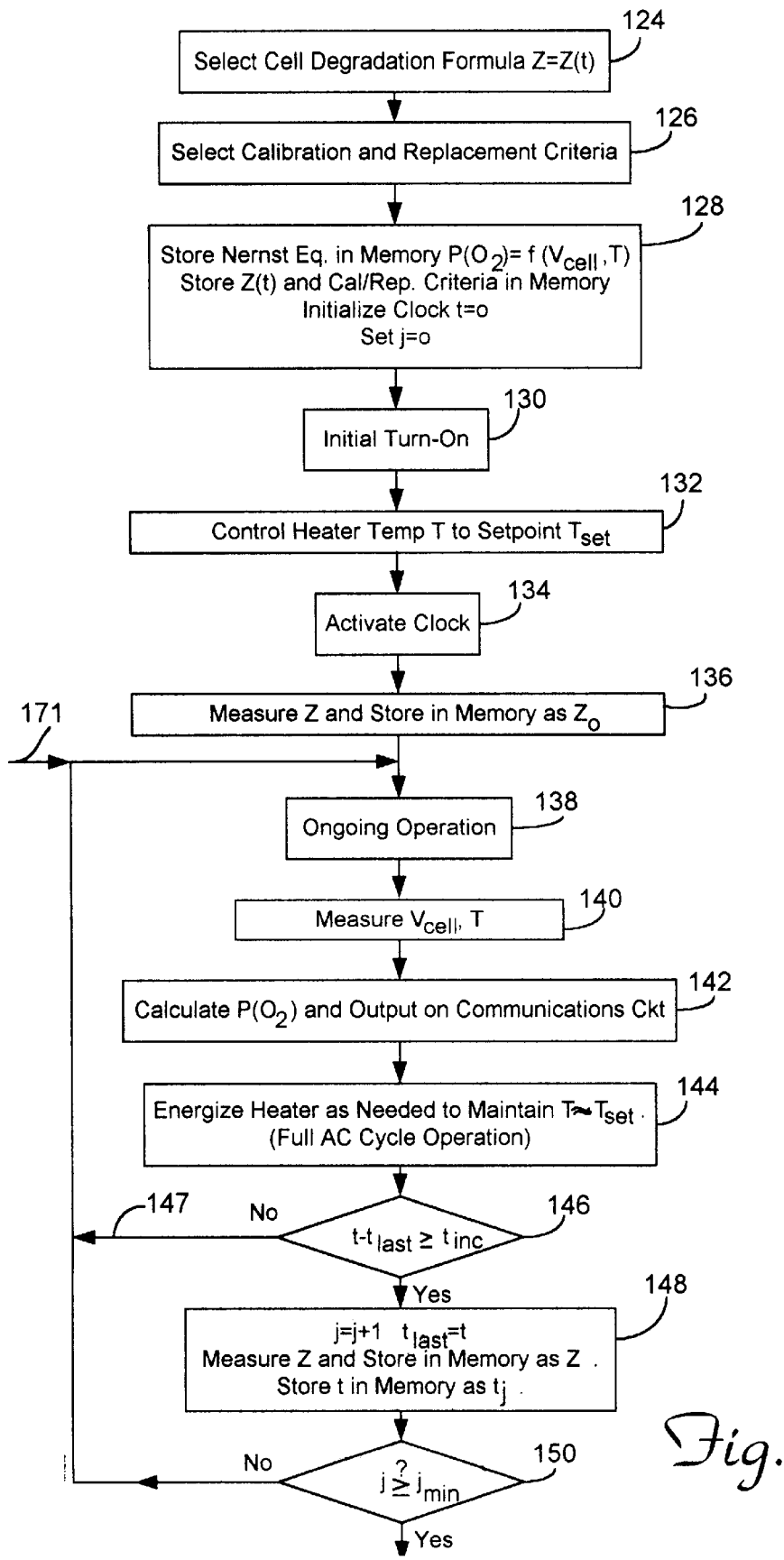
FIGS. 3a and 3b are flow diagrams showing a preferred method of operating a gas analyzer for diagnostic purposes.
Figure 3B:
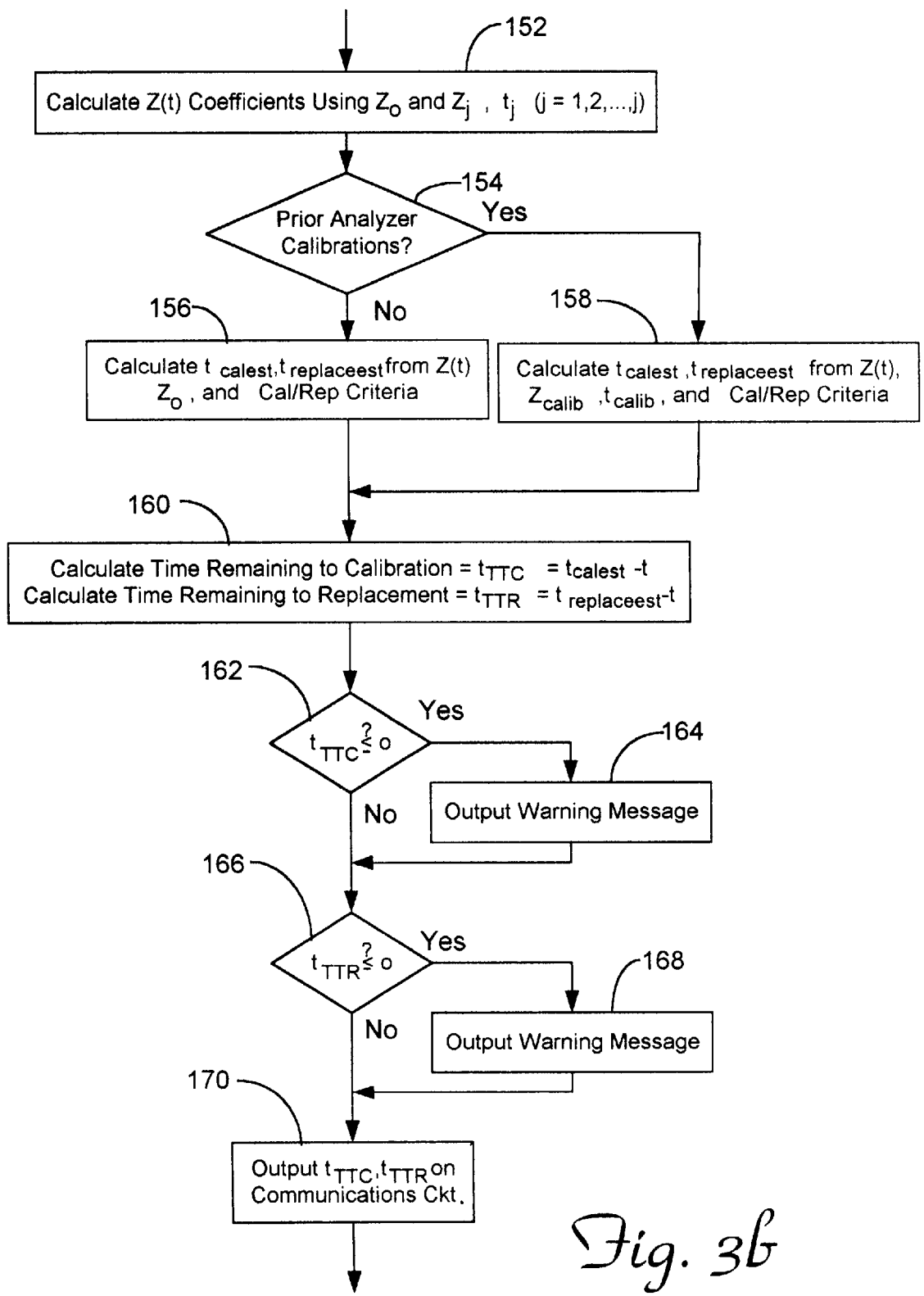

FIGS. 3a and 3b show a preferred method of operating the analyzer 40 according to the invention. At step 124, a model cell impedance function Z(t) such as that of Equation 6 is selected for the particular solid electrolyte cell to be used. Alternately the selected Z(t) can be a generalized function such as a truncated polynomial in t with unknown coefficients. Calibration and replacement criteria such as those of Equations 2 and 4 are selected at step 126. Such criteria and the function Z(t) are stored in analyzer memory 118 at step 128. The Nernst or other equation that calculates $P(O_2)$ from measured values $V_{cell}$ and T is also stored in memory 118. Clock 120 which counts elapsed time t is zeroed, as is a counter j. When the user first installs the analyzer 40 in a duct and provides power to it at 130, and after controller 94 controls the heater temperature T to a setpoint $T_{set}$ stored in memory 118 at step 132, clock 120 is activated at 134 and at step 136 the cell impedance Z is measured and stored in memory 118 as the initial impedance value $Z_0$. Thereafter, for ongoing operation 138 of the analyzer, the cell output $V_{cell}$ and temperature T are measured at 140 followed by calculating at step 142 the flue oxygen level $P(O_2)$ from the Nernst or similar equation and communicating such level to the remote site by communications circuit 122. Heater circuit 92 energizes cell heater 66 to maintain heater and cell temperature T at $T_{set}$ as shown at step 144. Decision block 146 gives rise to intermittent measurement of the cell diagnostic parameter. The difference between the actual elapsed time t and a time $t_{last}$ when the cell diagnostic was last measured is compared to a time $t_{inc}$ representing how often to measure the cell impedance. $t_{inc}$ can be set to any desired value but values between 1 hour and 1 day are preferred to permit operation without an excessive amount of memory 118 to store each (t,Z) data point. If a diagnostic check was performed within the last $t_{inc}$ then control returns via line 147 to ongoing operation box 138. Otherwise, step 148 is performed. Counter j is incremented by 1, the parameter $t_{last}$ is set to the current time t, cell impedance is measured and stored as $Z_j$ along with the current time t as $t_j$. Decision block 150 returns operation to ongoing operation box 138 if the number of stored impedance values is less than a number $j_{min}$. Otherwise operation continues at step 152 (see FIG. 3b) Analyzer circuit 50 performs a least squares, fuzzy logic, or other suitable mathematical operation to calculate the coefficients of Z(t) that cause Z(t) to most closely fit the measured data points $(t_j, Z_j)$, j=0 to j. If Z(t) is that of Equation 6, the coefficients to be calculated are a and b. If the analyzer has had no prior calibrations then operation passes through decision box 154 to step 156, where the analyzer circuit calculates an estimated calibration time $t_{calest}$ and an estimated replacement time $t_{replaceest}$ from the function Z(t), the initial impedance $Z_0$, and the calibration and replacement criteria respectively. If prior calibrations have been performed then step 158 can additionally use the measured cell impedance from most recent calibration $Z_{calib}$ and the corresponding time $t_{calib}$ in calculating $t_{calest}$ and $t_{replaceest}$. Operation then proceeds to step 160. Analyzer circuit 50 subtracts the present elapsed time t from $t_{calest}$ and $t_{replaceest}$ to yield an estimated time remaining to calibration $t_{TTC}$ and an estimated time remaining to replacement $t_{TTR}$ respectively. If $t_{TTC}$ is negative then decision block 162 directs operation to step 164 where a warning message or flag indicating the analyzer is in need of calibration is output over communication circuit 122. Likewise if $t_{TTR}$ is negative decision block 166 reverts control to step 168 where a warning message or flag indicating the analyzer is in need of replacement is output over communication circuit 122. At step 170 both $t_{TTC}$ and $t_{TTR}$ are output on communication circuit 122 to the remote location, and operation reverts via line 171 to ongoing operation box 138. If both $t_{TTC}$ and $t_{TTR}$ are non-negative, circuit 122 can provide an additional indication that the analyzer output is (likely) within the accuracy specification (e.g. 3% of reading).

Figure 4:
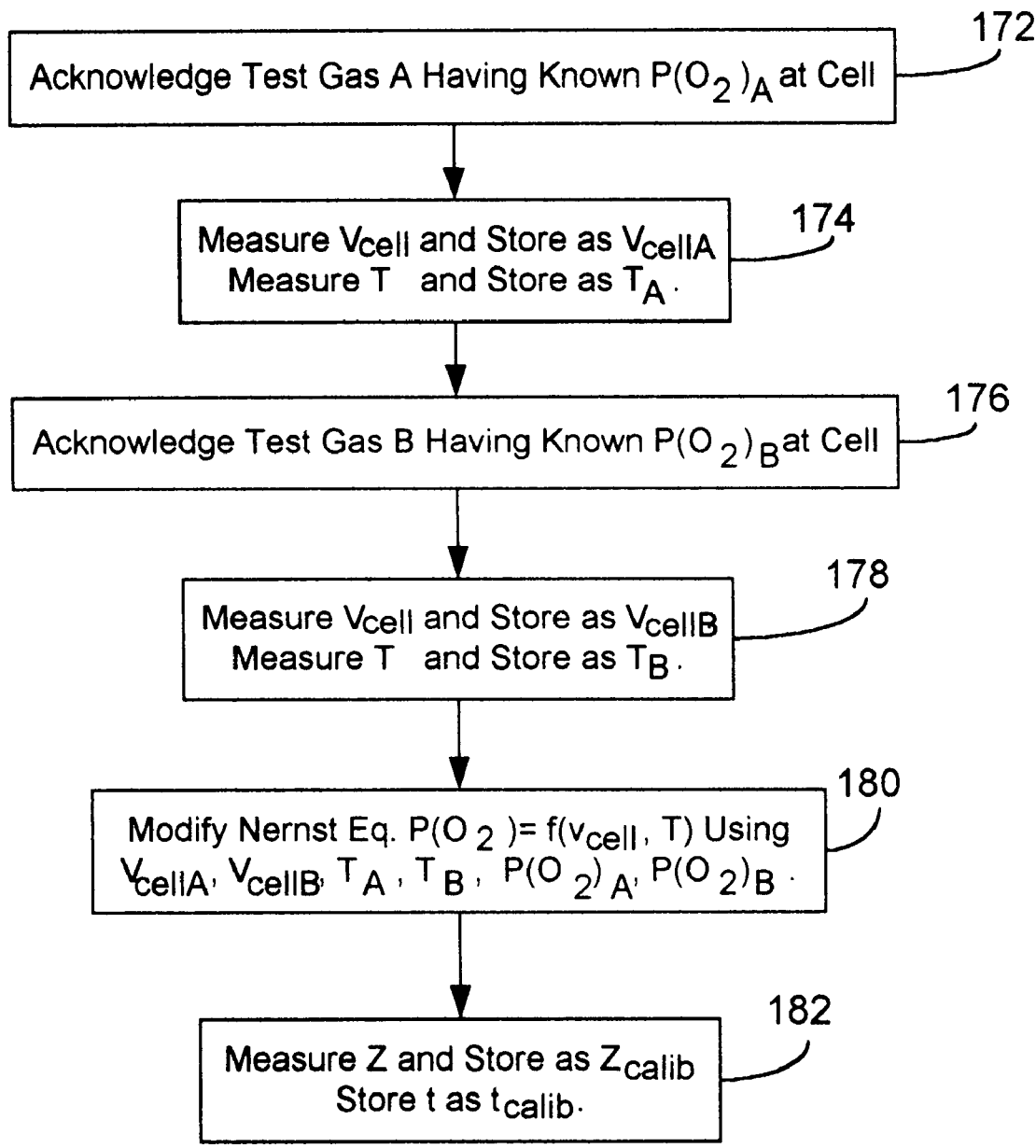
FIG. 4 is a flow diagram of a preferred calibration procedure.

When analyzer circuit 50 generates the warning message of step 164 recommending sensor calibration, a calibration operation as shown in FIG. 4 can be executed either manually or automatically. After exposing the solid electrolyte cell to test gas A having a known oxygen content $P(O_2)_A$, the operator sends an acknowledgment to analyzer circuit 50 at step 172. The analyzer circuit then measures cell output $V_{cell}$ and temperature T at step 174 and stores the measured values as $V_{cellA}$ and $T_A$. Circuit 50 then waits for an acknowledgment at step 176 that a test gas B having a different oxygen content $P(O_2)_B$ has been introduced to the cell. When acknowledgment is received, $V_{cell}$ and T are again measured and stored this time as $V_{cellB}$ and $T_B$ in step 178. At step 180 the analyzer circuit revises the Nernst or other equation so that the cell output calculated from such equation agrees with the new calibration data. The cell impedance Z is measured and stored as $Z_{calib}$ with the present time stored as $t_{calib}$ at the final step 182.

Figure 5:
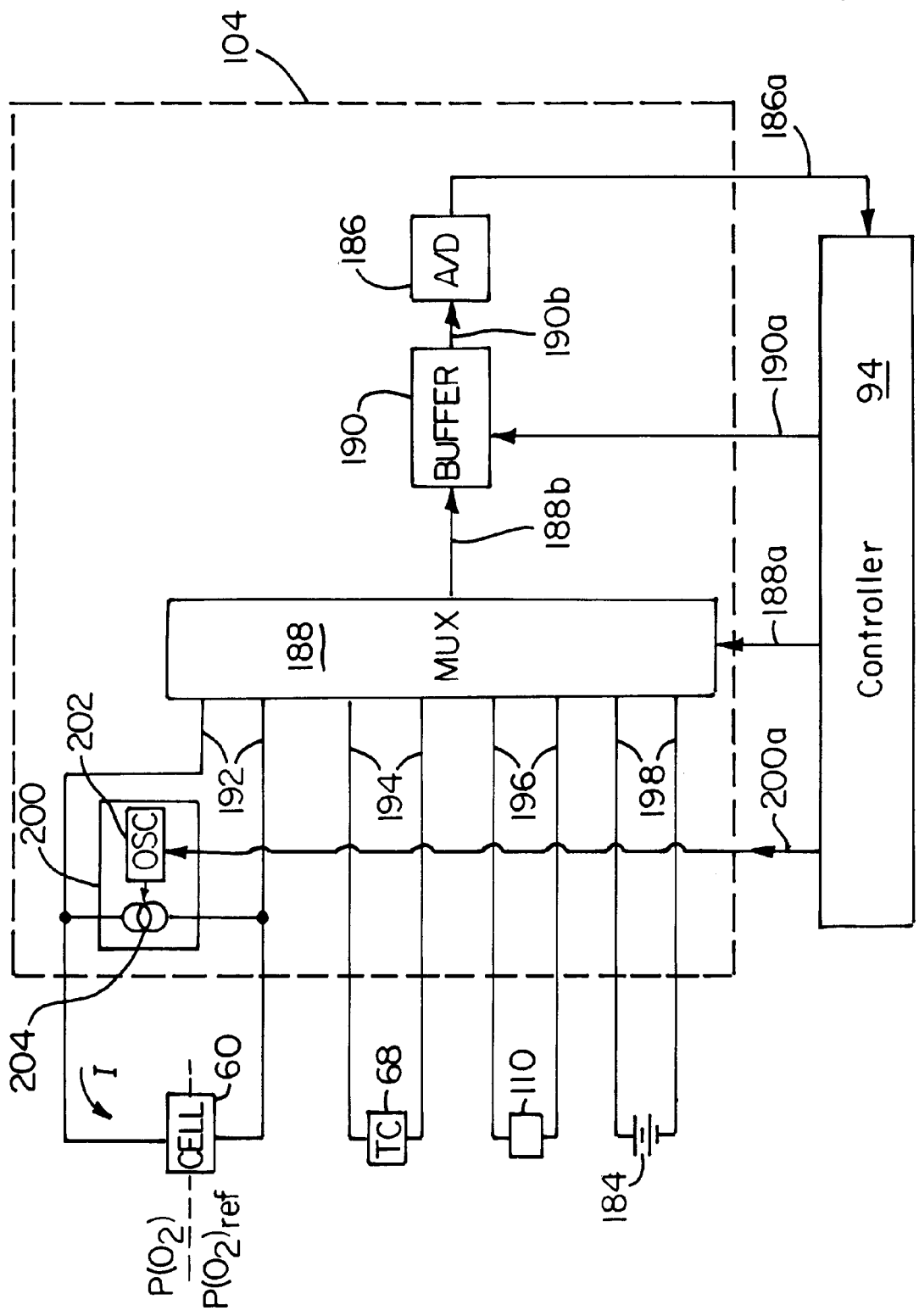
FIG. 5 is a block diagrammatic schematic of a portion of the preferred analyzer circuit including a measurement circuit having a diagnostic circuit.

Returning now to the preferred design of analyzer circuit 50, the block diagram of FIG. 5 shows the controller 94, the measurement circuit 104, and connections therebetween. Measurement circuit 104 receives an EMF input signal from solid electrolyte cell 60, thermocouple 68, local temperature sensor 110, and a DC voltage reference 184 and couples such inputs to an analog-to-digital (A/D) converter 186. The inputs couple to the A/D converter 186 through a multiplexer (MUX) 188 and a high input impedance buffer amplifier 190 as shown. To make a measurement, controller 94 directs MUX 188 via line 188a to connect one of the input line pairs 192, 194, 196, or 198 to a MUX output on line 188b. Buffer 190 amplifies the MUX output with a gain that is preferably programmable by controller 94 over line 190a. A/D converter 186 receives the buffer 190 output over line 190b and transmits a digital value representative of the selected input 192, 194, 196, or 198 to controller 94 over line 186a. The programmable gain of buffer circuit 190 gives measurement circuit 104 added versatility in measuring a wide range of input levels.

The measurement circuit 104 preferably includes a diagnostic circuit 200 coupled in parallel with cell 60 across input lines 192. When directed by controller 94 over control line 200a, an oscillator 202 within diagnostic circuit 200 activates a current source 204 at one or more selected frequencies. The current source directs a known current I through cell 60. By comparing the voltage across input lines 192 before and during activation of diagnostic circuit 200, the controller 94 can calculate the potential difference ΔV caused by the current I and thereby calculate cell impedance Z from $Z=\Delta V/I$. Note that this diagnostic check is performed on cell 60 while the analyzer 40 is in situ—the analyzer probe is installed in the duct and the cell 60 is exposed to flue gas. This is possible because the measured impedance of solid electrolyte cells 60 is substantially independent of the cell output $V_{cell}$ and of the oxygen levels $P(O_2)$ and $P(O_2)_{ref}$. An important benefit of such in situ diagnostic measurement over other techniques is the ability to assess the cell condition with minimal disturbance of the normal analyzer operation. In an alternate embodiment diagnostic circuit 200 can vary the level of current I until a specified potential difference $\Delta V$ is achieved. In that case Z is again calculated from $Z=\Delta V/I$.

Figure 6:
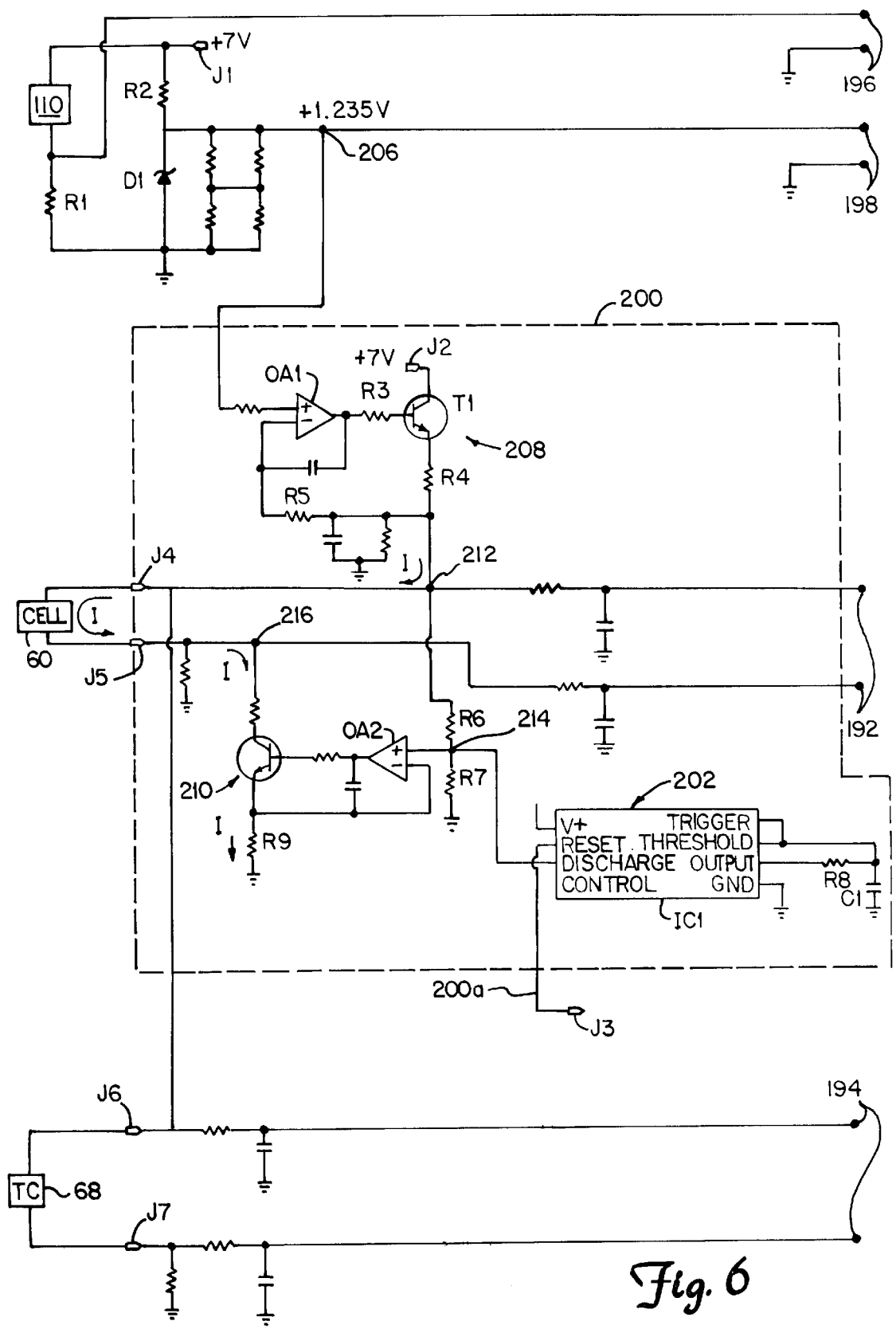
FIG. 6 is a schematic of a portion of a preferred measurement circuit having a diagnostic circuit useable in a solid electrolyte gas analyzer.

A preferred diagnostic circuit 200 and associated measurement circuitry is shown in greater detail in FIG. 6. Inputs to the circuit are the cell 60, thermocouple 68, and local temperature sensor 110. Also input to the circuit are various DC voltages obtained directly or indirectly from switching power supply 84, which DC voltages are used to power analyzer circuit components including amplifiers OA1 and OA2, and a 555-series timer IC1 which functions as oscillator 202. Power supply 84 supplies 7 VDC to jumpers J1 and J2. Sensor 110 (Analog Devices model AD590) passes a known current as a function of temperature through a known series resistor R1. The resulting potential across R1, indicative of the temperature inside the electronics housing, is relayed via input lines 196 to MUX 188. A zener diode D1 in series with a resistor R2 generates a DC reference potential at node 206, preferably about 1.235 VDC. This reference potential is relayed via input lines 198 to MUX 188 and is used to verify the accuracy of A/D converter 186. In preferred circuit 200, the current source 204 shown in FIG. 5 comprises a current source circuit 208 and a current sink circuit 210. Node 206 couples the reference potential to current source circuit 208 which comprises operational amplifier OA1 connected as shown to feedback elements resistor R3, transistor T1, resistor R4, and resistor R5. In steady state operation when diagnostic circuit 200 is essentially inactive, transistor T1 is essentially off except that it is activated as required to maintain node 212 at the reference potential of node 206. Current sink circuit 210 couples to node 212 via a voltage divider comprising series resistors R6, R7. Node 214 between resistors R6 and R7 couples to the non-inverting input of operational amplifier OA2 and also to a DISCHARGE output from timer IC1. Timer IC1 is controlled by a RESET input that connects via a jumper J3 to the controller 94, preferably through a buffer circuit. While controller 94 keeps RESET in a LO (grounded) state, the IC1 output at DISCHARGE is at ground potential. When controller 94 changes the RESET input to a HI state, the DISCHARGE output alternates between ground and an open circuit state at a particular frequency set by a resistor R8 and a capacitor C1. A frequency of about 50 to 150 Hz has been found effective to provide a reliable diagnostic indication.

Current sink circuit 210 draws current I through cell 60, which current is supplied by current supply circuit 208, only when DISCHARGE output of IC1 is in an open state. In such instance the potential at non-inverting node 214 becomes the reference potential times (R7)/(R6+R7), and the selection of a drain resistor R9 on the drain of transistor T2 controls the amount of current I drawn through cell 60 from current source circuit 208. In a preferred embodiment R6=R7, making the potential at node 214 half the reference potential, i.e. 0.618V, and R9=620 Ω so that I≈1 milliampere. Such current level is high enough to generate an easily measurable potential difference $\Delta V$ across cell 60 for anticipated cell impedances (approx. 10 to 250 Ω), but not so high that significant ohmic heating can occur in cell 60. Solid electrolyte cell 60 connects via jumpers J4, J5 to nodes 212, 216 which couple to current supply circuit 208 and current sink circuit 210, and also to input lines 192 leading to MUX 188.

Thermocouple 68 connects via jumpers J6, J7 to input lines 194 leading to MUX 188, with the connection at jumper J6 held at the potential of node 212.

Figure 7:
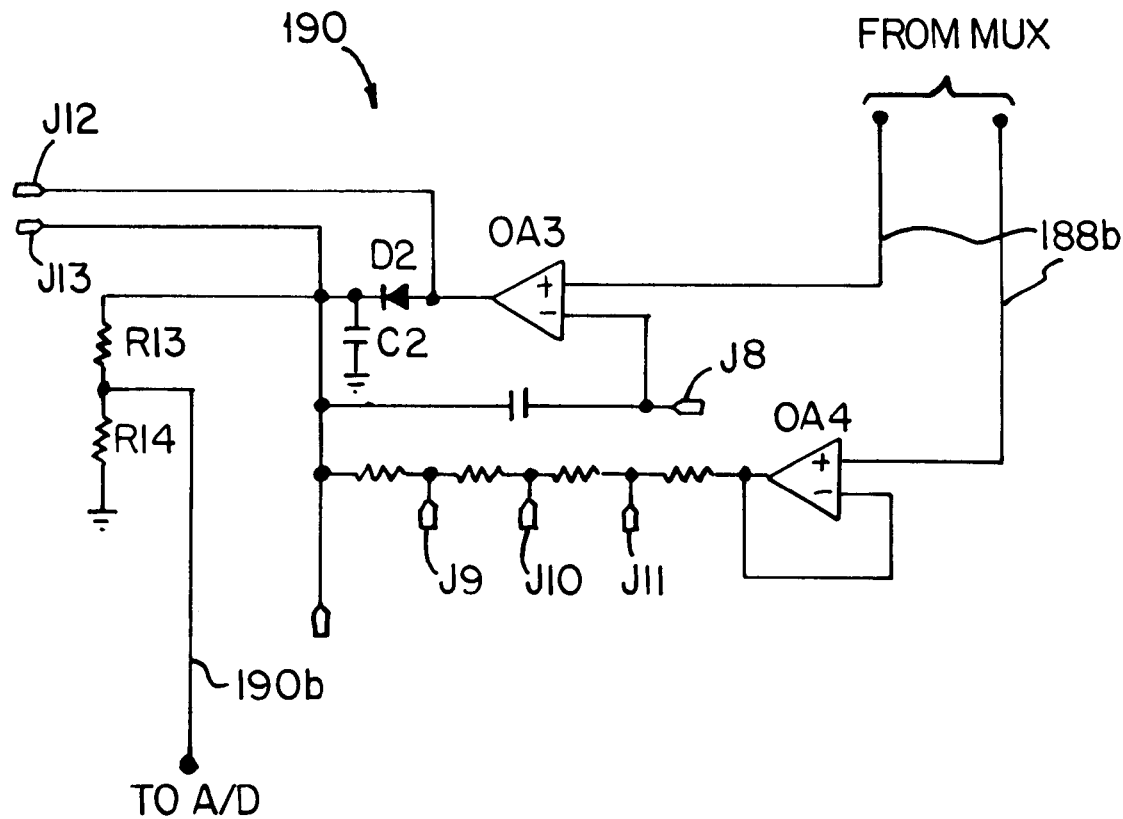
FIG. 7 is a schematic of a buffer amplifier circuit of a measurement circuit useable in a solid electrolyte gas analyzer in accordance with the preferred embodiment.

FIG. 7 shows details of preferred buffer amplifier circuit 190 introduced in FIG. 5. Lines 188b, 188b carry the output from MUX 188 to high input impedance amplifiers OA3 and OA4, both powered directly, or indirectly through intermediate DC voltage converters, by switching power supply 84. Amplifier OA4 is configured as a follower amplifier and OA3 is configured to have selectable gain and peak tracking capability. Gain selection is accomplished using jumpers J8, J9, J10, J11 which connect to controller 94. Controller 94 selects low, medium, or high gain by connecting J8 selectively to J9, J10, or J11 respectively such that the feedback resistance for OA3 is R10, R10+R11, or R10+R11+R12 respectively. Peak tracking is accomplished using jumpers J12, J13 which can connect directly or indirectly to controller 94. Ordinarily peak tracking is disabled by shorting jumpers J12, J13 together. However when controller 94 energizes diagnostic circuit 200 it also decouples J12 from J13, permitting capacitor C2 to charge through diode D2 to track the peak voltage level $V_{cell}+\Delta V$ due to the modulated current I pumped through cell 60. Line 190b connects between resistors R13 and R14 and carries the buffer amplifier output to A/D converter 186.

FIG. 8a depicts a voltage signal observed on input lines 192 which couple to the cell 60 and diagnostic circuit 200. Prior to a time $t_\alpha$ the signal is at a potential $V_{cell}$ generated solely by the heated cell 60. At time $t_\alpha$ controller 94 activates diagnostic circuit 200, sending modulated current I through cell 60 such that the potential difference $\Delta V$ from the current flowing through the cell impedance Z adds to the cell output $V_{cell}$. Also at time $t_\alpha$ controller 94 decouples jumpers J12, J13 so that buffer circuit 190 can transmit a stable peak voltage of $V_{cell}+\Delta V$ to A/D converter 186. Diagnostic circuit 200 remains activated long enough for buffer circuit 190 to stabilize and A/D converter 186 to provide a reliable output on line 186a. Controller 94 then turns diagnostic circuit 200 off at time $t_\beta$, where $t_\beta-t_\alpha\approx1$ millisecond, and the signal level returns to $V_{cell}$. Controller 94 compares the A/D converter output between time $t_\alpha$ and $t_\beta$ with the output just prior to $t_\alpha$ to obtain $\Delta V$ and thereby calculate the cell diagnostic parameter Z. Diagnostic circuit 200 remains inactive until controller 94 automatically activates it again at a time $t_\alpha+t_{inc}$. Since $t_{inc}$ can be hours or even days, the cell output $V_{cell}$ may be different from its value at $t_\alpha$ due to a change in temperature T or oxygen level $P(O_2)$.

Although the diagnostic circuit of FIG. 6 that generates the signal of FIG. 8a is a preferred embodiment because of its simplicity and low number of circuit components required, alternate in situ diagnostic techniques can be used that will generate different signals. For example the polarity of the current I can be reversed so that $\Delta V$ subtracts from rather than adds to $V_{cell}$. FIG. 8b shows still another technique wherein current I is a sinusoid of the selected frequency and $\Delta V$ is measured peak-to-peak. Both the sinusoidal current corresponding to FIG. 8b and the square-wave modulated current corresponding to FIG. 8a are substantially single-frequency for purposes of measuring cell impedance Z even though the square-wave current has small amplitude high frequency components. If desired, cell impedance Z can be monitored at two or more frequencies by switching one or more resistors in place of resistor R8 or one or more capacitors in place of capacitor C1, thereby changing the frequency of oscillator 202.

Although the present invention has been described with reference to preferred embodiments, workers skilled in the art will recognize that changes can be made in form and detail without departing from the spirit and scope of the invention as defined by the claims appended hereto. The invention pertains to solid electrolyte gas analyzers but does not encompass the solid electrolyte cell itself, which can have various configurations and compositions.

What is claimed is:

1. A gas analyzer having a solid electrolyte cell and a heater disposed proximate the cell, the cell providing a cell output as a function of a gas of interest, the gas analyzer providing an analyzer output as a function of the cell output and comprising:

a heater circuit coupled to the heater to heat the cell in response to a control signal;

a temperature sensitive device operably coupled to the cell and adapted to provide a temperature sensitive device output related to temperature of the cell;

a measurement circuit coupled to the cell and including a diagnostic circuit to measure an impedance of the cell and provide a diagnostic output indicative of a cell degradation condition while the cell is exposed to the gas of interest;

a controller coupled to the diagnostic circuit adapted to intermittently activate the diagnostic circuit, receive the temperature sensitive device output, and provide the control signal to the heater circuit to maintain the cell at an elevated temperature; and a memory circuit adapted to store diagnostic information relating cell impedance to cell degradation, and wherein the diagnostic output is related to the diagnostic information and cell impedance.

2. The analyzer of claim 1, wherein the diagnostic circuit measures the cell impedance at a predetermined frequency.

3. The analyzer of claim 2, wherein the predetermined frequency is between about 50 and 150 Hz.

4. The analyzer of claim 1, wherein the diagnostic circuit injects a predetermined electrical current through the cell and measures an electrical potential across the cell.

5. The gas analyzer of claim 1, wherein the memory circuit is adapted to store therein cell calibration criterion information and wherein the diagnostic output indicates a time when the cell is required to be serviced based on a function of the cell calibration criterion information.

6. The gas analyzer of claim 5, wherein the service indicated is recalibration of a cell.

7. The gas analyzer of claim 5, wherein the service indicated is replacement of the cell.

8. In a gas analyzer having a solid electrolyte cell heated by a heater and coupled to an analyzer circuit, the solid electrolyte cell providing a cell output as a function of a gas of interest, the improvement wherein the analyzer circuit comprises:

a heater circuit coupled to the heater;

a temperature sensitive device operably coupled to the cell and the heater circuit to maintain the solid electrolyte cell at an elevated temperature sensed by the temperature sensitive device;

a memory having cell related diagnostic information stored therein; and a controller for controlling the memory to provide an analyzer output indicating the condition of the solid electrolyte cell as a function of a measured impedance and selected diagnostic information in the memory, said controller being operably coupled to an output of said temperature sensitive device.

9. The gas analyzer of claim 8, wherein the cell related diagnostic information comprises information relating to cell degradation, cell calibration and cell replacement.

10. A method of detecting a condition of a solid electrolyte cell providing a cell EMF in response to an amount of constituent in a gas of interest exposed to the cell, the method comprising the steps of:

(a) maintaining the cell at an elevated temperature;

(b) measuring the cell EMF and providing as a function thereof an analyzer output indicative of the amount of constituent;

(c) measuring a cell diagnostic parameter while the cell is exposed to the gas of interest and maintained at the elevated temperature and providing as a function thereof a diagnostic output indicative of the condition of the cell;

(d) storing in memory a mathematical model of the cell diagnostic parameter as a function of time;

(e) revising the mathematical model using the measured cell diagnostic parameter; and (f) using the revised mathematical model to generate the diagnostic output.

11. The method of claim 10, wherein the cell diagnostic parameter is an impedance of the cell and wherein the second measuring step includes the steps of injecting a known current through the cell and measuring a voltage change resulting from such known current.

12. The method of claim 11, wherein the known current is modulated at a predetermined frequency.

13. The method of claim 12, wherein the frequency is between about 50 and 150 Hz.

14. The method of claim 12, wherein the known current is injected such that the voltage change and the cell EMF have the same polarity.

15. The method of claim 10, further comprising the step of:

(g) providing a calibration criterion that defines a condition of the cell diagnostic parameter associated with a degradation of the cell EMF beyond a specified accuracy limit;

wherein the using step (f) includes using the revised mathematical model to calculate a calibration time when the calibration criterion will be met and wherein the diagnostic output is a function of the calibration time.

16. The method of claim 10, further comprising the step of:

(g) providing a replacement criterion that defines a condition of the cell diagnostic parameter associated with an unacceptable degradation of the cell;

wherein the using step includes using the revised mathematical model to calculate a replacement time when the replacement criterion will be met and wherein the diagnostic output is a function of the replacement time.

17. The method of claim 10 including the step of using the revised mathematical model to generate an output determining whether cell recalibration is indicated.

18. The method of claim 10 including using the diagnostic output to determine whether cell replacement is indicated.

* * * * *

UNITED STATES PATENT AND TRADEMARK OFFICE
CERTIFICATE OF CORRECTION

PATENT NO. : 5,980,728
DATED : November 9, 1999
INVENTOR(S) : Boris Y. Farber et al.

It is certified that error appears in the above-identified patent and that said Letters Patent is hereby corrected as shown below:

<u>Title page,</u>
Under Item [73], Assignee: replace "Rosemont Analytical Inc." with -- Rosemount Analytical Inc. --

Signed and Sealed this

Nineteenth Day of February, 2002

Attest:

JAMES E. ROGAN
Attesting Officer  Director of the United States Patent and Trademark Office